United States Patent [19]
Abdulrazik

[11] Patent Number: 5,789,240
[45] Date of Patent: Aug. 4, 1998

[54] DIFFUSION CELL FOR EX-VIVO PRESSURE-CONTROLLED TRANSCORNEAL DRUG PENETRATION STUDIES

[76] Inventor: Mohammad Abdulrazik, POB 31821, Jerusalem 91317, Israel

[21] Appl. No.: 715,926

[22] Filed: Sep. 19, 1996

[30] Foreign Application Priority Data

Sep. 21, 1995 [IL] Israel ............................. 115390

[51] Int. Cl.$^6$ ............................................. C12M 3/00
[52] U.S. Cl. ........................... 435/284.1; 435/286.1; 435/286.6; 435/287.1; 435/297.1
[58] Field of Search ................. 435/284.1, 286.1, 435/286.6, 287.1, 289.1, 297.1

[56] References Cited

U.S. PATENT DOCUMENTS

| | | | |
|---|---|---|---|
| 4,667,504 | 5/1987 | Hobson | 73/38 |
| 4,686,190 | 8/1987 | Cramer et al. | 435/291 |
| 5,030,575 | 7/1991 | Stofac | 435/296 |
| 5,141,873 | 8/1992 | Steudl et al. | 436/148 |
| 5,591,636 | 1/1997 | Grass | 435/287.1 |

*Primary Examiner*—David A. Redding
*Attorney, Agent, or Firm*—Edward Langer, Pat. Atty.

[57] ABSTRACT

A diffusion cell for ex-vivo transcorneal drug penetration studies. The diffusion cell design enables control of the pressure and the flow in the acceptor chamber, and can be used for in-vitro studies of the effect of intraocular pressure on transcorneal drug penetration. Validation tests were carried out and reproducible results of the transcorneal drug penetration experiments were obtained with a practical experiment protocol.

18 Claims, 6 Drawing Sheets

DIFFUSION CELL FOR EX-VIVO PRESSURE-CONTROLLED TRANSCORNEAL DRUG PENETRATION STUDIES

FIELD OF THE INVENTION

The present invention relates to medical laboratory testing equipment and the like, and more particularly, to a diffusion cell designed to simulate the eye anterior chamber anatomy by enabling pressure and flow control, to assist in transcorneal drug penetration studies.

BACKGROUND OF THE INVENTION

In the early stages of new opthalmic drug development, the medical research community fully recognizes the important role that ex-vitro experiments have in the evaluation of the transcorneal penetration of topically-applied opthalmic drugs, and in elucidating the mechanism of such penetration. Elucidation of the mechanism be which a topically-applied drug penetrates the cornea can contribute to the research efforts devoted to enhance ocular drug penetration and bioavailability by developing new ophthalmic vehicles and dosage forms.

The prior art contains several diffusion cells with different designs used in transcorneal drug penetration studies. All of the prior art diffusion cells overlook important physiological factors that may alter transcorneal penetration, such as intraocular pressure. In all the ex-vitro transcorneal drug penetration studies published in the scientific literatures no transcorneal tension was used. In the normal human eye there is a constant intraocular pressure of 10–22 mm Hg greater than atmospheric pressure with diurnal variation of 2–3 mm Hg.

It is known that the transcorneal penetration of topically-applied opthalmic drug is poor, and that only a small portion (5–10%) of the drug penetrates the cornea. The prior art provides no data about the effect of intraocular pressure on transcorneal drugs penetration. It is very complicated to obtain such data from in-vivo experiments, particularly for comparative kinetic studies.

Thus, it would be desirable to provide a diffusion cell which deals with transcorneal tension. Such a diffusion cell can be an excellent basis for an ex-vitro model for studies of the effect of intraocular pressure on transcorneal drugs penetration, to enable routine kinetic studies with physiological transcorneal tension.

SUMMARY OF THE INVENTION

Accordingly, it is a principal object of the present invention to overcome the disadvantages of prior art techniques and provide a diffusion cell which simulates the eye anterior chamber anatomy, thus allowing for more accurate studies of the effect of intraocular pressure on transcorneal drugs penetration.

In the ex-vitro experiments described herein, fresh excised animal corneas, usually albino rabbit corneas, are used since intraocular pressure in the rabbit eye is similar to humans.

The inventive diffusion cell is designed to simulate the eye anterior chamber anatomy, with the excised cornea horizontally positioned above a sealed acceptor chamber formed with controlled inlet and outlet orifices connected to a manometer, with an open donor chamber provided above the acceptor chamber. This design enables one to control the pressure in the acceptor chamber, with or without flow. The bottom wall of the open donor chamber can be provided shaped either with a curved edge, allowing drugs accumulation above the cornea, or shaded flat, allowing excess drug material to flow away. The diffusion cell can be provided in several diameters. The chosen diameter assures complete covering of the scleral edge and minimal covering of the cornea.

Other unique features of the inventive diffusion cell:

1. Pressure regulator, allowing automatic maintaining of pressure in the acceptor chamber with fixed acceptor chamber volume.
2. High-accuracy automatic pump (microliter range) with controlled diffusion cell inlet and outlet valves, allowing constant flow of very low volumes against fixed pressure with fixed volume in the acceptor chamber.
3. Optional temperature, oxygenation and humidity control hood.
4. Adjustable low volume of the acceptor chamber.
5. Adjustable depth of fluid beneath the cornea.
6. Unique design enables easy and quick mounting of the excised cornea.
7. The epithelial surface of the cornea can be in contact with fresh air.

The last two preceding features are important for maintaining viability of the cornea. In validation tests, the durability of the sealing in the acceptor chamber was proved, by injection of air at a pressure of 200 mmHg into the acceptor chamber as the diffusion cell, with a mounted rabbit cornea, was kept under water in a vessel. No air bubble was detected during a 120 minute period.

Other features and advantages of the invention will become apparent from the following drawings and description.

BRIEF DESCRIPTION OF THE DRAWINGS

For a better understanding of the invention with regard to the embodiments thereof, reference is made to the accompanying drawings, in which like numerals designate corresponding elements or sections throughout, and in which.

DETAILED DESCRIPTION OF THE PREFERRED EMBODIMENT

Figure 1:
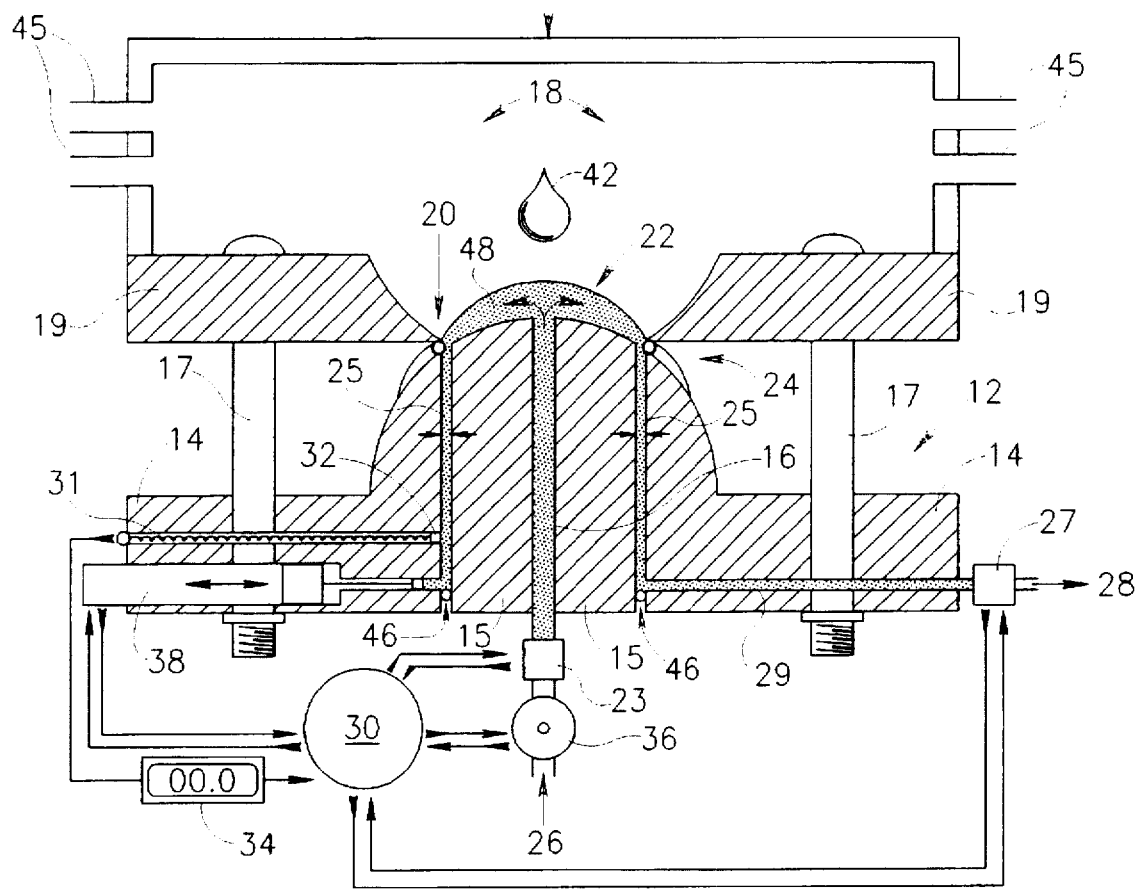
FIG. 1 is a cross-sectional elevation view of a diffusion cell constructed and operated in accordance with the principles of the present invention.

Referring now to FIG. 1, there is shown a cross-sectional elevation view of a diffusion cell 10 constructed and operated in accordance with the principles of the present invention. Diffusion cell 10 comprises an acceptor chamber 12 provided by a base portion 14 having a central hole within which there is seated a movable, donut-shaped central portion 15 having a central orifice 16. Vertically extending screws 17 pass through base portion 14, for tightening thereto a ring-shaped wall 19 defining a donor trough 18. Diffusion cell 10 can be constructed so as to be available in any diameter.

At the top of central acceptor chamber portion 15 a sealing O-ring 20 is mounted (in cross-section), which allows good sealing between base portion 14 and a cornea 22 mounted thereon, when screws 17 tighten ring-shaped wall 19 against base portion 14. The central portion 15 is chosen such that the maximum diameter of sealing ring 20 is slightly smaller than the limbal diameter of the cornea 22 in order to keep the scleral rim 24 thereof outside the interface of sealing ring 20.

The excised cornea 22 with scleral rim 24 is positioned over central portion 15, beneath open donor trough 18, defined be ring-shaped wall 19. A circumferential gap 25 is defined between central portion 15 and base portion 14. Gap 25 communicates with controlled inlet 26 and outlet 28 ports, via central orifice 16 and exit orifice 29, and inlet and outlet valves 23, 27. The volume defined beneath cornea 22 is filled with acceptor chamber fluid 48. Fluid 48 enters acceptor chamber 12 via inlet valve 23, orifice 16, and circulates beneath cornea 22, and then exits chamber 12 via circumferential gap 25, exit orifice 29, and valve 27.

A central control unit 30 is connected via wire 31 to pressure transducer 32, which measures pressure in mm Hg, and displays the measurement on readout 34. Control unit 30 controls a high-accuracy pump 36, a pressure regulator 38 and inlet and outlet valves 23,27. Four screws 17 close the cell firmly. Drug droplet 42 is applied over the central part of cornea 22. The donor trough 18 can be opened to the room air, or optionally covered with a temperature, oxygenation and humidity control hood 44, with appropriate connections 45. An additional O-ring 46 seals the bottom end of gap 25 between the acceptor chamber base portion 14 and central portion 15, preventing leakage of fluid 48 from acceptor chamber 12.

Figure 2A:
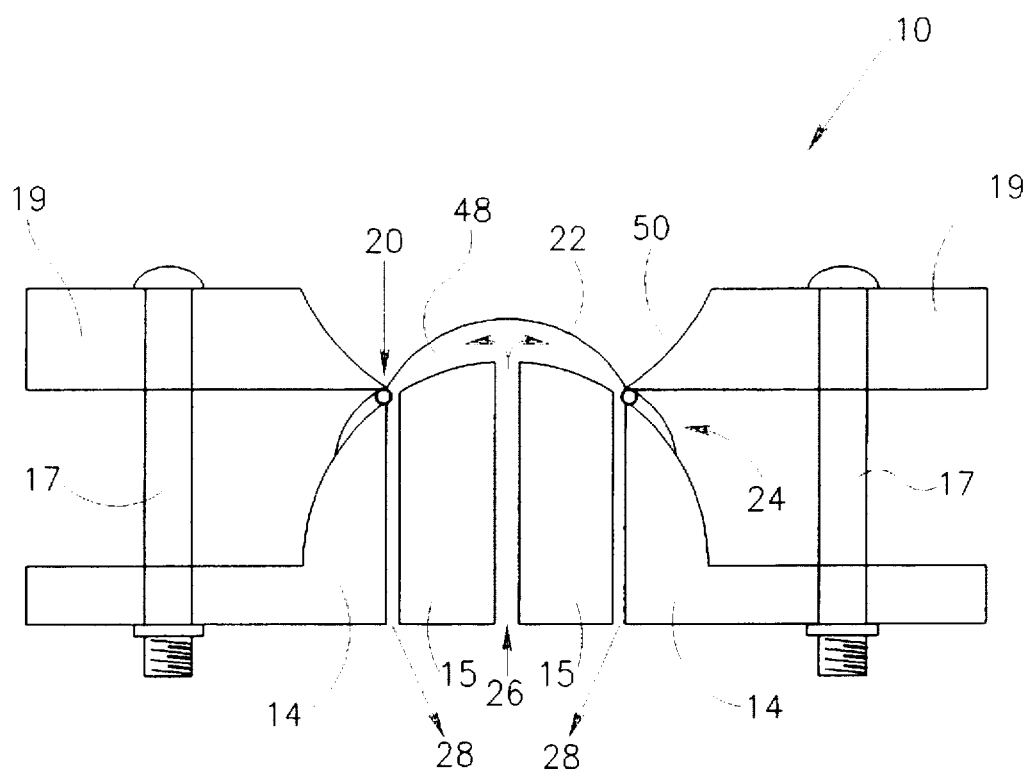
FIGS. 2a–b are elevation views of alternative embodiments of the diffusion cell, respectively, with a curved edge or flat donor chamber shade.
Figure 2B:
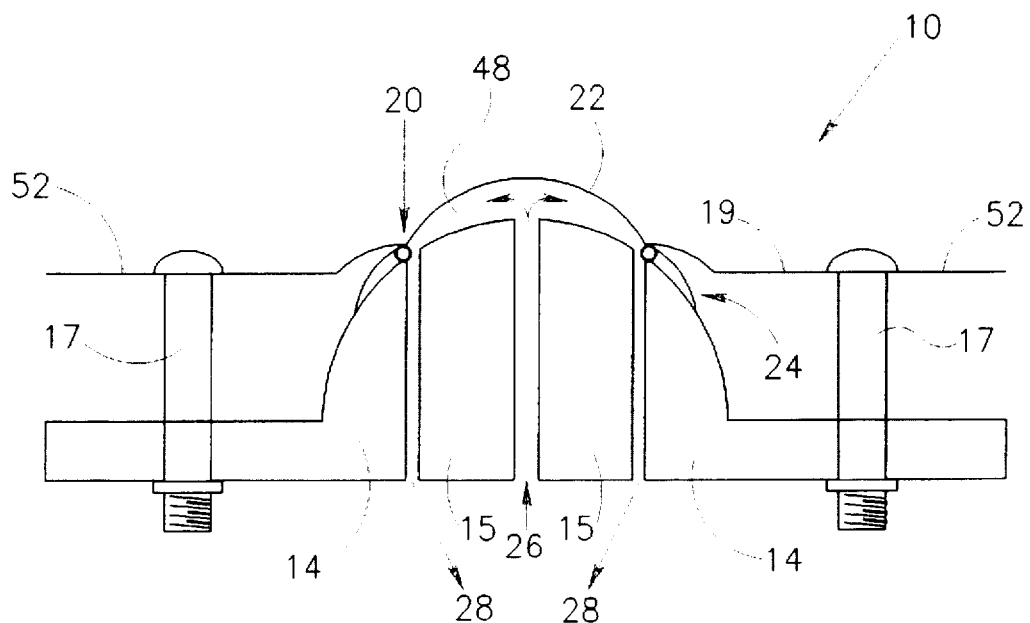

Referring now to FIGS. 2a–b, ring-shaped wall 19 can be formed either with a curved edge 50, allowing drug accumulation above cornea 22, or flat 52, allowing excess drugs material to flow away. Central portion 15 is movable vertically with respect to base portion 14. The diameter of central orifice 16 and gap 25 between the fixed, base portion 14 of acceptor chamber 12 and movable, central portion 15 can be designed with small dimensions, enabling acceptor chamber fluid 48 to occupy a small volume.

Figure 3:
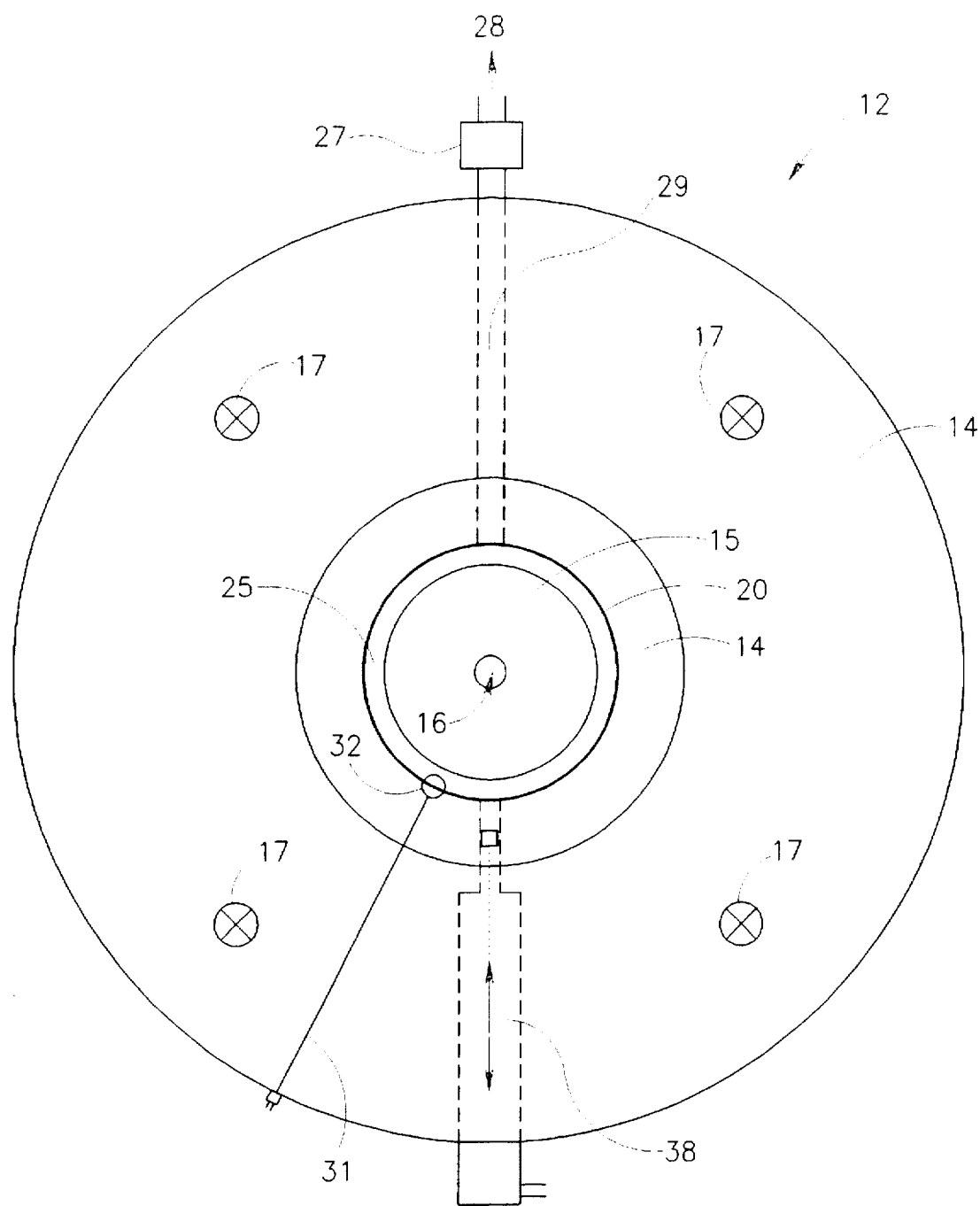
FIG. 3 is a top view of the acceptor chamber portion.

Referring now to FIG. 3, there is shown a top view of acceptor chamber 12. Acceptor chamber fluid 48 enters chamber 12 via central orifice 16, and exits via circumferential gap 25 between the fixed, base portion 14 and the central, movable, portion 15 of the acceptor chamber 12. O-ring 20 is also shown, as well as other construction details according to FIG. 1.

Figure 4:
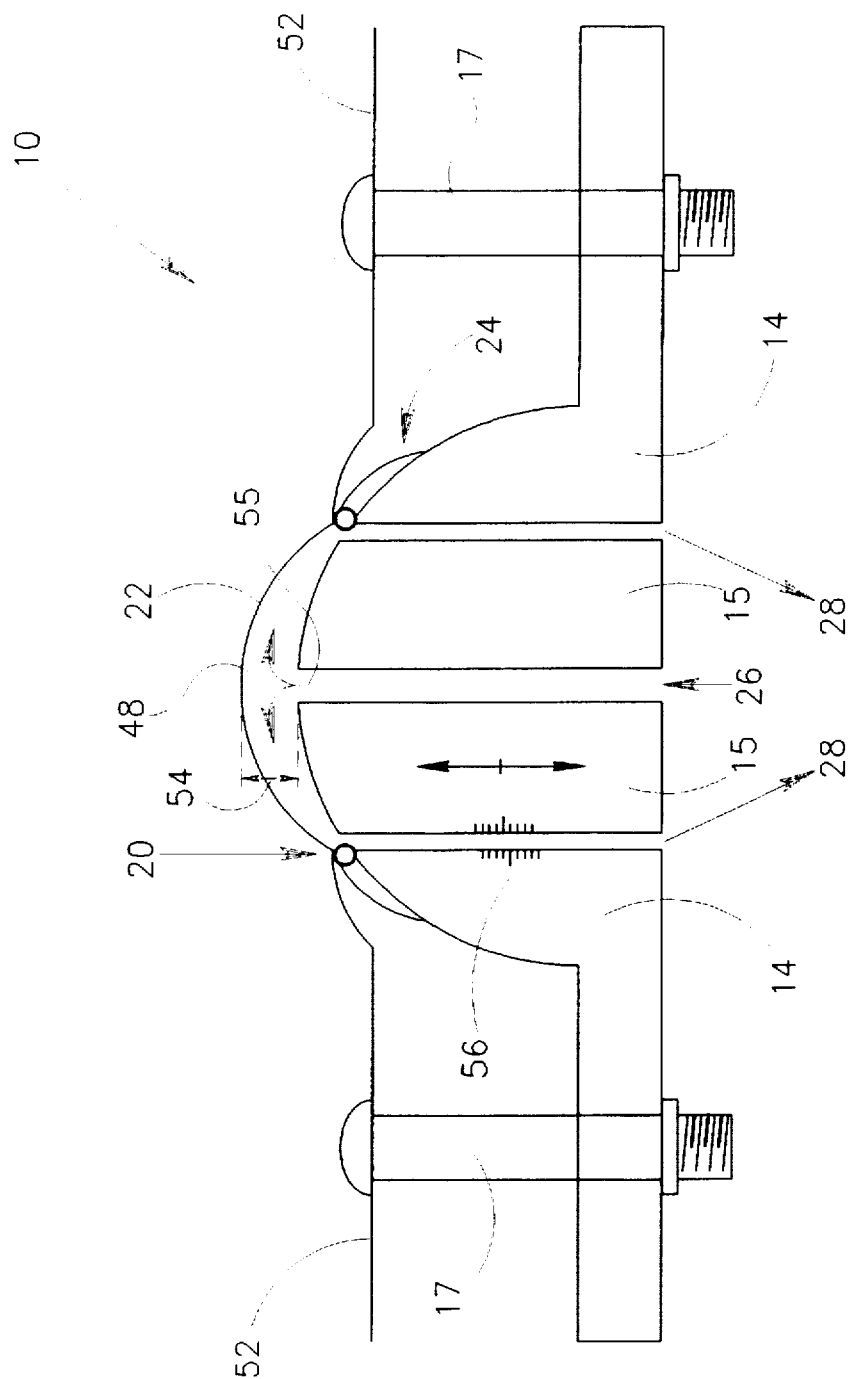
FIG. 4 is an elevation view of the diffusion cell showing further construction details.

Referring now to FIG. 4, there is shown in an elevation view of the diffusion cell 10, revealing further construction details. The depth 54 of the fluid 48 trapped beneath the cornea 22 is adjustable, and a reference scale 56 is provided to indicate the position of movable, central portion 15 within fixed base portion 14. The direction of fluid flow in the acceptor chamber 12 beneath the cornea 22 is indicated by the arrows at 55.

Figure 5:
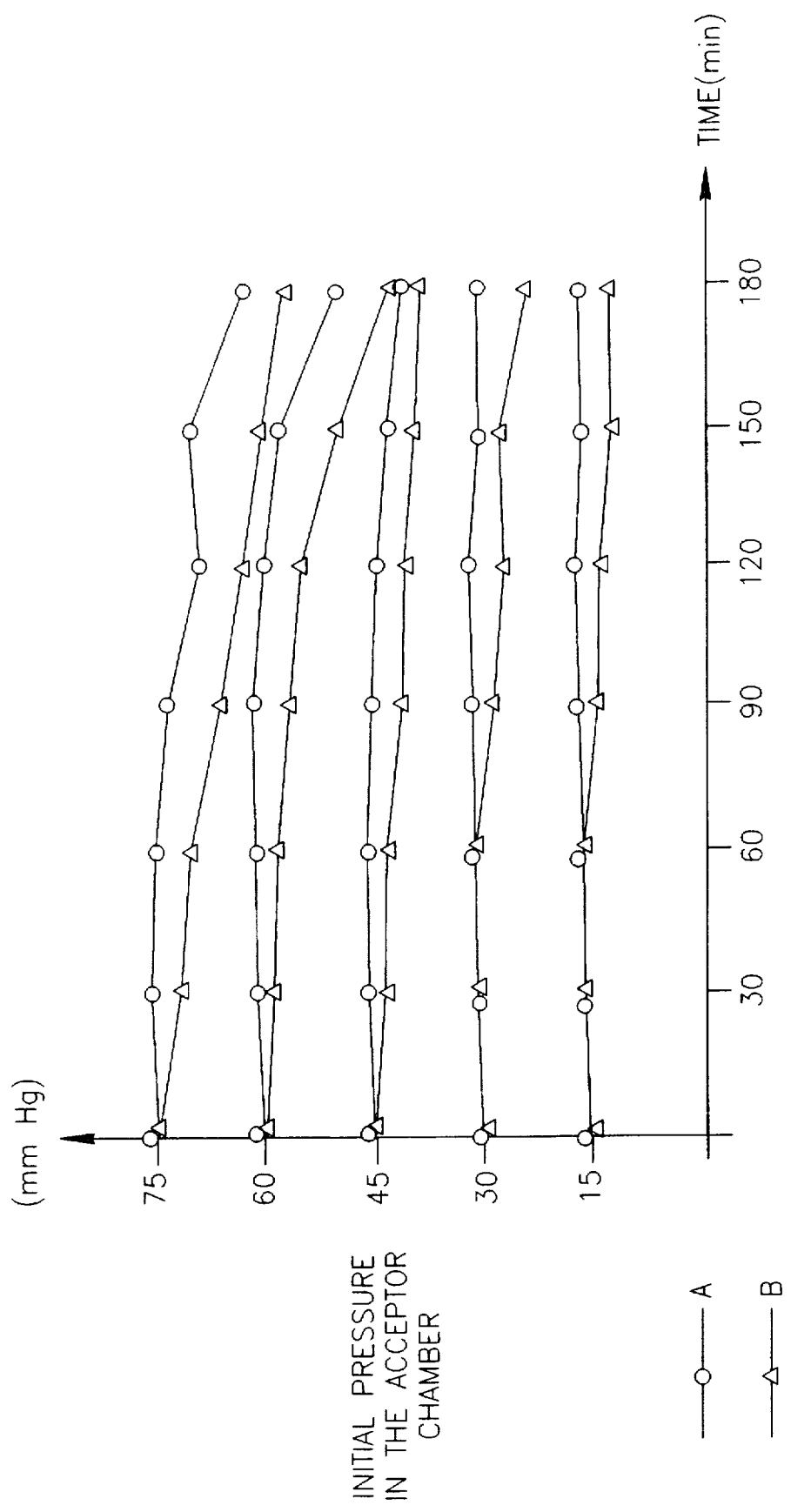
FIG. 5 is a graph of the pressure level in the acceptor chamber over time.

Referring now to FIG. 5, there is shown a graph of the pressure level in the acceptor chamber over time. This data refers to the durability of acceptor chamber 12 in maintaining the pressure therein over time at five different acceptor chamber pressures, with (Graph A) or without (Graph B) continuous wetting of the cornea 22.

Figure 6:
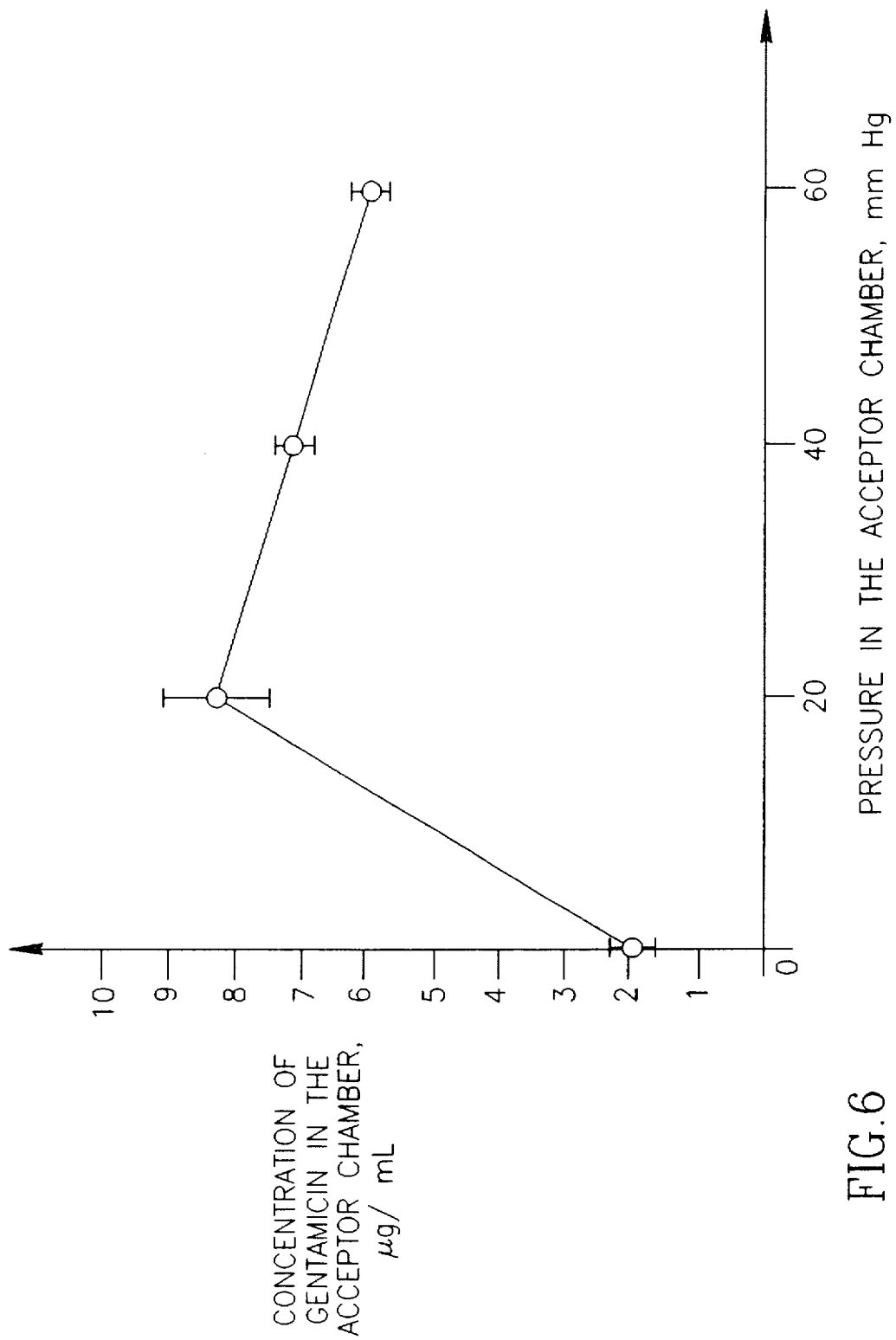
FIG. 6 is a graph of drug penetration experimental results based on use of the inventive diffusion cell.

Referring now to FIG. 6, there is shown a graph of the results of transcorneal drugs penetration experiments based on use of the inventive diffusion cell, as now described.

EXPERIMENT PROTOCOL

Albino rabbits (2.5 kg males) were sacrificed for the experiment and their eyes enucleated. The conjunctiva and external structures were removed, and the sclera was cut circumferentially at the equator of the eye. Then, the lens and the iris diaphragm were removed. The endothelium was washed gently with a balanced salt solution (BSS) to remove vitreous and tissue debris, and the epithelial surface was kept wet continuously.

The fresh excised cornea with scleral rim was mounted with the endothelium surface facing the acceptor chamber 12. An acceptor chamber 12 with a top diameter of 1–2 mm less than the limbal diameter of the cornea was used, in order to keep the sclera outside the sealing interface. After good positioning of the cornea was achieved, the four screws 17 (FIG. 1) were closed firmly.

BSS-plus (manufactured by Alcon) was injected gently through the inlet valve 23 of the acceptor chamber 12. Air bubbles were expelled before pressure build-up to the desirable level, with the help of the adjustable inlet and outlet valves 23, 27. Pump 36 (FIG. 1) is operated if flow is mandatory (the normal flow in the human eye is 2 microliter/min.). The use of the built-in pressure regulator 38 (FIG. 1) maintains the pressure at the desirable level with constant volume of acceptor chamber 12, and its use is recommended in experiments longer than 90 minutes, carried out without continuous wetting of the cornea.

Before starting the drug penetration experiment, a comparative measurement of the pressure in the acceptor chamber 12 was carried out with a Schiotz tonometer. If there is no pressure loss, the drug is applied over the center of the epithelial surface of cornea 22 and the experiment begins, with the desired temperature oxygenation and humidity conditions. After the planned time period, the experiment was terminated.

The donor trough fluid was collected, the acceptor chamber 12 was opened and its fluid was collected, with volume measurement. Both the donor trough 18 and the acceptor chamber 12 fluids were sent separately for drug level analysis. The central portion of the cornea was trephined using a trephine with the same diameter as the top O-ring 20 diameter of the acceptor chamber. The trephined corneal button and the reminder tissue rim were sent separately for drug level analyses.

In other experiments an hydration test was performed: the trephined corneal button was weighed, thereafter dried overnight at 50 deg C., then weighed again and the hydration level was calculated. When the hydration level was greater than 80%, the experimental results were disqualified.

In the current series of experiments, no flow was provided in the acceptor chamber and the pressure regulator 38 was not utilized. The experiment was carried out at room temperature with fresh air and without further oxygenation. The cornea was not wetted continuously. The average volume of the acceptor chamber fluid was 0.5 ml. The durability of pressure maintenance in the acceptor chamber (per the graph of FIG. 5) was satisfactory over a 120 min. time period, up to 60 mm Hg pressure range. The viability of the cornea, measured by the hydration test and histology, was satisfactory under the same conditions.

The results of the ex-vivo transcorneal drug penetration experiment are shown in the graph of FIG. 6. In this experiment, one microliter of gentamicin as sulfate 4% was dropped on the center of the epithelial surface of the mounted cornea at various pressure levels of acceptor chamber (0, 20, 40, 60 mm Hg). After 60 minutes, the concentration of gentamicin in the acceptor chamber was measured. The results have shown that the best penetration was achieved at acceptor chamber pressure of 20 mm Hg, with less penetration at higher pressure levels. When the pressure in the acceptor chamber was lowered to the zero level, the penetration was poor.

It will be appreciated that in addition to trans-epithelial penetration experiments through the cornea as above, diffusion cell 10 can be utilized to carry out trans-endothelial penetration experiments into the cornea. These experiments are carried out by adding the drugs to the acceptor chamber fluid 48, and measuring the quantity of drugs passing the endothelial surface of the cornea, into the cornea or through the cornea to the donor trough 18. Thus, bi-directional studies are possible.

In conclusion, the experimental results indicate that the transcorneal tension should not be overlooked when routine ex-vivo transcorneal drugs penetration experiments are carried out, and the fluctuations in intra-ocular pressure may have an interesting effect on the transcorneal penetration of topically-applied opthalmic drugs. Thus, the present invention provides a suitable practical model for investigating the effect of intra-ocular pressure on transcorneal drugs penetration.

Having described the invention with regard to certain specific embodiments thereof, it is to be understood that the description is not meant as a limitation, since further modifications may now suggest themselves to those skilled in the art, and it is intended to cover such modifications as fall within the scope of the appended claims.

I claim:

1. A diffusion cell for ex-vivo transcorneal drug penetration studies, comprising:

an acceptor chamber having a fixed base portion formed with an opening and a vertically movable central portion seated in said opening so as to define a circumferential gap therebetween, said acceptor chamber having seated over a top end thereof in sealing fashion an excised cornea, said sealed acceptor chamber having inlet and outlet ports communicating with said gap, said inlet and outlet ports having controllable valves for controlling pressure in said acceptor chamber under flow and non-flow conditions;

a ring-shaped wall extending horizontally above said sealed acceptor chamber and having a centrally disposed aperture formed therein through which an epithelial surface of the excised cornea is exposed; and means for measuring and controlling said sealed acceptor chamber pressure, said controlled pressure being applied against an endothelial surface of the excised cornea facing said sealed acceptor chamber, to develop a controllable transcorneal tension level, said diffusion cell enabling transcorneal drug penetration studies under controllable transcorneal tension levels.

2. The diffusion cell of claim 1, further characterized in that said aperture is formed on a lower side of a donor trough extending substantially vertically from said aperture and having a concave cross-sectional profile, allowing drug accumulation above the cornea.

3. The diffusion cell of claim 1, wherein said aperture and said ring shaped wall form a substantially flat surface, allowing excess drug accumulation above the cornea to flow away.

4. The cell of claim 1 wherein said acceptor chamber pressure measuring means comprises a pressure transducer.

5. The cell of claim 1 wherein said acceptor chamber is filled up with an acceptable balanced salt solution.

6. The diffusion cell of claim 1 wherein said acceptor chamber has a diameter suitable to the diameter of any cornea.

7. The diffusion cell of claim 1 further comprising a pump before the inlet valve, and a central flow control unit controlling both said inlet and outlet valves and said pump, to enable constant flow of low fluid volumes through said acceptor chamber, at a fixed volume and pressure.

8. The diffusion cell of claim 1 further comprising a regulator to regulate said pressure without changing said acceptor chamber fluid volume, said regulator being operated when a precise pressure in said acceptor chamber is mandatory for a prolonged time period.

9. The diffusion cell of claim 1 wherein movement of said central portion provides adjustment of the depth of fluid beneath the cornea and said pressure in said sealed acceptor chamber.

10. The diffusion cell of claim 1, further comprising a hood over said wall for maintaining temperature, oxygenation and humidity control in a volume above the cornea enclosed by said hood.

11. The diffusion cell of claim 10 wherein said sealed acceptor chamber pressure is controllable under flow and non-flow conditions.

12. A diffusion cell for bi-directional transepithelial and transendothelial ex-vivo transcorneal and into-corneal drug penetration studies, comprising:

an acceptor chamber having a fixed base portion formed with an opening and a vertically movable central portion seated in said opening so as to define a circumferential gap therebetween, said acceptor chamber having seated over a top end thereof in sealing fashion an excised cornea, said sealed acceptor chamber having inlet and outlet ports communicating with said gap, said inlet and outlet ports having controllable valves for controlling pressure in said acceptor chamber under flow and non-flow conditions;

a ring-shaped wall extending horizontally above said sealed acceptor chamber and having a centrally disposed aperture formed therein through which an epithelial surface of the excised cornea is exposed; and means for measuring and controlling said sealed acceptor chamber pressure, said controlled pressure being applied against an endothelial surface of the excised cornea facing said sealed acceptor chamber, to develop a controllable transcorneal tension level, said diffusion cell enabling transcorneal drug penetration studies under controllable transcorneal tension levels.

13. The diffusion cell of claim 12, further characterized in that said aperture is formed on a lower side of a donor trough extending substantially vertically from said aperture and having a concave cross-sectional profile, allowing drug accumulation above the cornea.

14. The diffusion cell of claim 12 wherein said donor trough holds a drug for application over said cornea epithelial surface.

15. The diffusion cell of claim 12 wherein said acceptor chamber holds a drugs for application through said cornea endothelial surface.

16. A diffusion cell for bi-directional trans-membrane material penetration studies comprising:

an acceptor chamber having a fixed base portion formed with an opening and a vertically movable central portion seated in said opening so as to define a circumferential gap therebetween, said acceptor chamber having seated over a top end thereof in sealing fashion an excised cornea, said sealed acceptor chamber having inlet and outlet ports communicating with said gap, said inlet and outlet ports having controllable valves for controlling pressure in said acceptor chamber under flow and non-flow conditions;

a ring-shaped wall extending horizontally above said sealed acceptor chamber and having a centrally disposed aperture formed therein through which an epithelial surface of the excised cornea is exposed; and means for measuring and controlling said sealed acceptor chamber pressure, said controlled pressure being applied against an endothelial surface of the excised cornea facing said sealed acceptor chamber, to develop a controllable transcorneal tension level, said diffusion cell enabling transcorneal drug penetration studies under controllable transcorneal tension levels.

17. The diffusion cell of claim 16 wherein said donor trough holds diffusable materials for application over said membrane and diffusion to said acceptor chamber.

18. The diffusion cell of claim 16 wherein said acceptor chamber holds diffusable materials for application through said membrane and diffusion to said donor trough.

* * * * *